US008017157B2

(12) United States Patent  
Yoo et al.

(10) Patent No.: US 8,017,157 B2  
(45) Date of Patent: Sep. 13, 2011

(54) METHOD OF TREATING A WOUND WITH ACIDIFIED PLASMA OR SERUM

(75) Inventors: Won Min Yoo, Seoul (KR); Kyung Hee Chang, Seoul (KR); Nae Choon Yoo, Seoul (KR); Ki Chang Keum, Seoul (KR); Sang Yup Lee, Daejeon (KR); Gene Lee, Yongin-si (KR)

(73) Assignee: Osiris Therapeutics, Inc., Columbia, MD (US)

( * ) Notice: Subject to any disclaimer, the term of this patent is extended or adjusted under 35 U.S.C. 154(b) by 905 days.

(21) Appl. No.: 11/638,056

(22) Filed: Dec. 12, 2006

(65) Prior Publication Data

US 2007/0148142 A1 Jun. 28, 2007

Related U.S. Application Data

(63) Continuation of application No. 10/508,841, filed on Sep. 21, 2004, now abandoned.

(30) Foreign Application Priority Data

May 9, 2003 (KR) .......................... 10-2003-00922

(51) Int. Cl.  
*A61K 35/16* (2006.01)
(52) U.S. Cl. .................................. 424/530; 424/531
(58) Field of Classification Search .................. None  
See application file for complete search history.

(56) References Cited

U.S. PATENT DOCUMENTS

| 4,006,220 A | 2/1977 | Gottlieb |
| 4,061,731 A | 12/1977 | Gottlieb |
| 4,141,973 A | 2/1979 | Balazs |
| 4,427,650 A | 1/1984 | Stroetmann |
| 4,427,651 A | 1/1984 | Stroetmann |
| 4,659,572 A | 4/1987 | Murray |
| 4,769,234 A | 9/1988 | Pines et al. |
| 4,808,576 A | 2/1989 | Schultz et al. |
| 4,842,305 A | 6/1989 | Kistenich et al. |
| 4,851,521 A | 7/1989 | Della Valle et al. |
| 4,863,897 A | 9/1989 | Dede et al. |
| 4,920,104 A | 4/1990 | DeVore et al. |
| 4,937,254 A | 6/1990 | Sheffield et al. |
| 4,937,270 A | 6/1990 | Hamilton et al. |
| 5,017,229 A | 5/1991 | Burns et al. |
| 5,017,900 A | 5/1991 | Ura et al. |
| 5,095,037 A | 3/1992 | Iwamitsu et al. |
| 5,149,691 A | 9/1992 | Rutherford |
| 5,165,938 A | 11/1992 | Knighton |
| 5,166,331 A | 11/1992 | Della Valle et al. |
| 5,183,805 A | 2/1993 | Lee et al. |
| 5,190,759 A | 3/1993 | Lindblad et al. |
| 5,196,185 A | 3/1993 | Silver et al. |
| 5,209,724 A | 5/1993 | Dhaliwal et al. |
| 5,234,914 A | 8/1993 | Gallina |
| 5,236,906 A | 8/1993 | Yamamoto |
| 5,356,683 A | 10/1994 | Egolf et al. |
| 5,358,973 A | 10/1994 | Lindblad et al. |
| 5,376,365 A | 12/1994 | Dikstein |
| 5,376,636 A | 12/1994 | Rutherford et al. |
| 5,409,904 A | 4/1995 | Hecht et al. |
| 5,432,167 A | 7/1995 | Brismar |
| 5,510,418 A | 4/1996 | Rhee et al. |
| 5,514,657 A | 5/1996 | Shoshan et al. |
| 5,520,926 A | 5/1996 | Ferguson |
| 5,529,987 A | 6/1996 | Gallina |
| 5,532,221 A | 7/1996 | Huang et al. |
| 5,550,112 A | 8/1996 | Gallina |
| 5,583,120 A | 12/1996 | Gallina |
| 5,585,007 A | 12/1996 | Antanavich et al. |
| 5,591,444 A | 1/1997 | Boss, Jr. |
| 5,604,200 A | 2/1997 | Taylor-McCord |
| 5,614,506 A | 3/1997 | Falk et al. |
| 5,624,915 A | 4/1997 | Gallina |
| 5,631,011 A | 5/1997 | Wadstrom |
| 5,631,241 A | 5/1997 | Della Valle et al. |
| 5,631,242 A | 5/1997 | Gallina |
| 5,639,738 A | 6/1997 | Falk et al. |
| 5,641,483 A | 6/1997 | Beaulieu |
| 5,663,160 A | 9/1997 | Meybeck et al. |
| 5,681,825 A | 10/1997 | Lindqvist et al. |
| 5,728,391 A | 3/1998 | Ikeya et al. |
| 5,731,298 A | 3/1998 | Reinmuller |
| 5,733,545 A | 3/1998 | Hood, III |
| 5,744,449 A | 4/1998 | Lipps et al. |
| 5,763,399 A | 6/1998 | Lee |
| 5,792,753 A | 8/1998 | Falk et al. |

(Continued)

FOREIGN PATENT DOCUMENTS

| CN | 1156042 | 8/1997 |
| CN | 1270812 | 10/2000 |
| EP | 0493985 A1 | 7/1992 |
| EP | 0497724 A1 | 8/1992 |
| FR | 2770779 | 5/1999 |
| JP | 03-240738 A | 10/1991 |

(Continued)

OTHER PUBLICATIONS

Hansson et al., "The Effect of Antiseptic Solutions on Microorganisms in Venous Leg Ulcers", Acta Derm Venereol (Stockh) 75 : 31-33 (1995).*  
Levenn et al., "Chemical Acidificaion of Wounds", Annals of Surger 178(6) : 745-753 (1973).*  
Kaufman et al., "Topical acidification promotes healing of experimental deep partial thickness skin burns: a randomized double-blind preliminary study", Burns 12 : 84-90 (1985).*  
Vodyannikova, "The Effect of Blood and its Components on the Healing Process in Experimental Freshy-Infected Wounds", Bulletin of Experimental Biology and Medicine 43 (1) : 101-104 (1957).*  
Makkaveev, "Equine blood serum as a tissue therapy preparation", Veterinariya 39 (1) :59-61 (1963) plus English abstract.*

(Continued)

*Primary Examiner* — Sandra Saucier  
(74) *Attorney, Agent, or Firm* — Ballard Spahr LLP

(57) ABSTRACT

The present invention relates to a pharmaceutical composition for the treatment of wounds containing blood plasma or serum and a method for treating wounds effectively by applying said composition to the wound site to normalize the tissue-environment around the site.

9 Claims, 1 Drawing Sheet

U.S. PATENT DOCUMENTS

| | | |
|---|---|---|
| 5,811,410 A | 9/1998 | Falk et al. |
| 5,817,642 A | 10/1998 | Falk et al. |
| 5,824,658 A | 10/1998 | Falk et al. |
| 5,827,834 A | 10/1998 | Falk et al. |
| 5,830,882 A | 11/1998 | Falk et al. |
| 5,834,444 A | 11/1998 | Falk et al. |
| 5,852,002 A | 12/1998 | Falk et al. |
| 5,866,554 A | 2/1999 | Shalaby et al. |
| 5,897,880 A | 4/1999 | Drizen et al. |
| 5,914,322 A | 6/1999 | Falk et al. |
| 5,925,656 A | 7/1999 | Kallam et al. |
| 5,942,498 A | 8/1999 | Falk et al. |
| 5,962,433 A | 10/1999 | Falk et al. |
| 5,972,906 A | 10/1999 | Asculai et al. |
| 5,977,088 A | 11/1999 | Harper et al. |
| 5,981,606 A | 11/1999 | Martin |
| 5,985,850 A | 11/1999 | Falk et al. |
| 5,990,095 A | 11/1999 | Falk et al. |
| 6,010,692 A | 1/2000 | Goldberg et al. |
| 6,022,866 A | 2/2000 | Falk et al. |
| 6,037,331 A | 3/2000 | Shalaby et al. |
| 6,048,844 A | 4/2000 | Falk et al. |
| 6,063,406 A | 5/2000 | Hornack |
| 6,069,135 A | 5/2000 | Falk et al. |
| 6,086,907 A | 7/2000 | Goldberg et al. |
| 6,087,344 A | 7/2000 | Falk et al. |
| 6,096,727 A | 8/2000 | Kuo et al. |
| 6,103,704 A | 8/2000 | Falk et al. |
| 6,114,314 A | 9/2000 | Falk et al. |
| 6,120,804 A | 9/2000 | Drizen et al. |
| 6,136,793 A | 10/2000 | Falk et al. |
| 6,140,312 A | 10/2000 | Falk et al. |
| 6,147,059 A | 11/2000 | Falk et al. |
| 6,165,978 A | 12/2000 | Rodgers et al. |
| 6,171,611 B1 | 1/2001 | Picciano |
| 6,194,392 B1 | 2/2001 | Falk et al. |
| 6,218,373 B1 | 4/2001 | Falk et al. |
| 6,232,303 B1 | 5/2001 | Callegaro et al. |
| 6,251,876 B1 | 6/2001 | Bellini et al. |
| 6,262,020 B1 | 7/2001 | Lezdey et al. |
| 6,271,216 B1 | 8/2001 | Mello et al. |
| 6,284,285 B1 | 9/2001 | Weis-Fogh |
| 6,294,202 B1 | 9/2001 | Burns et al. |
| 6,335,034 B1 | 1/2002 | Drizen et al. |
| 6,387,407 B1 | 5/2002 | Drizen et al. |
| 6,387,413 B1 | 5/2002 | Miyata et al. |
| 6,495,148 B1 | 12/2002 | Abbiati |
| 6,509,322 B2 | 1/2003 | Benedetti et al. |
| 6,521,223 B1 | 2/2003 | Calias et al. |
| 6,541,460 B2 | 4/2003 | Petito |
| 6,573,249 B2 | 6/2003 | Lezdey et al. |
| 6,596,703 B1 | 7/2003 | Seed et al. |
| 6,627,620 B1 | 9/2003 | Nielsen |
| 6,635,267 B1 | 10/2003 | Miyoshi et al. |
| 6,699,471 B2 | 3/2004 | Radice et al. |
| 6,723,345 B2 | 4/2004 | Drizen et al. |
| 6,828,308 B2 | 12/2004 | Mastradonato et al. |
| 6,838,448 B2 | 1/2005 | Ponzin |
| 6,924,273 B2 | 8/2005 | Pierce |
| 7,015,198 B1 | 3/2006 | Orentreich et al. |
| 7,132,412 B2 | 11/2006 | Petrigini et al. |
| 7,157,080 B2 | 1/2007 | Radice et al. |
| 2002/0025921 A1 | 2/2002 | Petito et al. |
| 2002/0068716 A1 | 6/2002 | Melmed et al. |
| 2002/0151466 A1 | 10/2002 | Hubbard et al. |
| 2002/0173485 A1 | 11/2002 | Mastradonato et al. |
| 2003/0007957 A1 | 1/2003 | Britton et al. |
| 2003/0124197 A1 | 7/2003 | Signore et al. |
| 2003/0147830 A1 | 8/2003 | Phillips et al. |
| 2003/0152639 A1 | 8/2003 | Britton et al. |
| 2003/0180390 A1 | 9/2003 | Keum et al. |
| 2003/0187381 A1 | 10/2003 | Greenawalt et al. |
| 2003/0211166 A1 | 11/2003 | Yamamoto et al. |
| 2003/0212005 A1 | 11/2003 | Petitio et al. |
| 2004/0019011 A1 | 1/2004 | Falk et al. |
| 2004/0092482 A1 | 5/2004 | Gupta |
| 2004/0180622 A1 | 9/2004 | Godfrey |
| 2004/0192643 A1 | 9/2004 | Pressato et al. |
| 2004/0197319 A1 | 10/2004 | Harch et al. |
| 2004/0242535 A1 | 12/2004 | Court et al. |
| 2004/0254143 A1 | 12/2004 | Mastradonato et al. |
| 2005/0107330 A1 | 5/2005 | Greve et al. |
| 2005/0129622 A1 | 6/2005 | Rault et al. |
| 2005/0136122 A1 | 6/2005 | Sadozai et al. |
| 2005/0136126 A1 | 6/2005 | Keum et al. |
| 2005/0142161 A1 | 6/2005 | Freeman et al. |
| 2005/0142208 A1 | 6/2005 | Yoo et al. |
| 2005/0147679 A1 | 7/2005 | Petito et al. |
| 2005/0180938 A1 | 8/2005 | Novelli |
| 2005/0181025 A1 | 8/2005 | Velebny et al. |
| 2005/0182022 A1 | 8/2005 | Pierce |
| 2005/0191286 A1 | 9/2005 | Gandy |
| 2005/0220882 A1 | 10/2005 | Pritchard et al. |
| 2005/0234011 A1 | 10/2005 | Mazzone et al. |
| 2005/0234013 A1 | 10/2005 | Parsons |
| 2005/0267068 A1 | 12/2005 | Back et al. |
| 2005/0272695 A1 | 12/2005 | Bach et al. |
| 2006/0040895 A1 | 2/2006 | Thacker |
| 2006/0069064 A1 | 3/2006 | Khaldoyanidi |
| 2006/0105991 A1 | 5/2006 | Ishikawa et al. |
| 2006/0121002 A1 | 6/2006 | Rolland et al. |
| 2006/0122147 A1 | 6/2006 | Wohlrab |
| 2006/0147393 A1 | 7/2006 | Macchi |
| 2006/0153893 A1 | 7/2006 | Matsuno et al. |
| 2006/0188578 A1 | 8/2006 | Fernandez et al. |
| 2006/0194759 A1 | 8/2006 | Eidelson |
| 2006/0258560 A1 | 11/2006 | Yang et al. |
| 2006/0293257 A1 | 12/2006 | Rosenbloom |
| 2007/0003505 A1 | 1/2007 | Carey |
| 2007/0048387 A1 | 3/2007 | Edwards et al. |
| 2007/0048391 A1 | 3/2007 | Keum et al. |
| 2007/0059377 A1 | 3/2007 | Freddo et al. |
| 2007/0087061 A1 | 4/2007 | Drake et al. |

FOREIGN PATENT DOCUMENTS

| | | |
|---|---|---|
| JP | 07-267992 A | 10/1995 |
| RU | 2082415 C1 | 6/1997 |
| WO | WO 86/03122 A1 | 6/1986 |
| WO | 9308811 | 5/1993 |
| WO | WO 94/22470 A1 | 10/1994 |
| WO | 9619982 | 7/1996 |
| WO | 9630038 | 10/1996 |
| WO | 0230432 A1 | 4/2002 |
| WO | 03094937 A1 | 11/2003 |
| WO | 2004028404 A2 | 4/2004 |

OTHER PUBLICATIONS

Allgöwer, M. et al., "Origin of Fibroblasts From Mononuclear Blood Cells: A Study on in Vitro Formation of The Collagen Precursor, Hydroxyproline, in Buffy Coat Cultures," Surgery, 47(4):603-610 (Apr. 1960).

Anonymous, "Arm & Hammer Peroxicare Baking Soda Toothpaste," Household Products Database from National Institutes of Health National Library of Medicine, pp. 1-3 (Mar. 2000). Online. Internet. Accessed on Apr. 14, 2011. http://hpd.nlm.nih.gov/cgbin/househole/brands?tbl=brands&id=2005032.

Anonymous, "Becaplermin Product Approval Information -- Licensing Action, Approvals 1-6" U.S. Food & Drug Administration, 1997, pp. 1-118; Online. Internet. Accessed on Apr. 14, 2011, http://www.fda.gov/cder/biologics/products/becaomj121697.htm.

Anonymous, "Becaplermin," Medline Plus, Feb. 1, 2009, pp. 1-3; Online. Internet. Accessed Apr. 15, 2011; www.nlm.nih.gov/ . . ./a699049.html.

Arm & Hammer, "Arm & Hammer ental Care Toothpaste Was Introduced Nationally in 1988," Arm & Hammer Milestones 150th Anniversary, p. 8 of 9 (1996). Online. Internet. Accessed Apr. 14, 2011, http://www.churchdwight.com/contact/downloads/cd150.pdf.

Baroni et al., "Sodium bicarbonate treatment reduces renal injury, renal production of dixorubicin-induced nephropathy," Am. J. Kidney Diseases, 34(2):328-337 (Aug. 1999).

Border W.A. et al., "Transforming Growth Factor-β in disease: The dark side of tissue repair," J. Clin. Invest., 90:1-7 (Jul. 1992).

Brown, P.D. et al., "Physicochemical activation of recombinant latent transforming growth factor-beta's 1, 2, and 3," Growth Factors, 3(1):35-43 (1990).

Den Tandt, W.R., "On the stability of human lysosomal enzymes at room temperature in normal and acidified plasma and serum," Clinica Chimica Acta 244: pp. 229-235 (1996).

DiCorleto, P.E. et al., "Cultured endothelial cells produce a platelet-derived growth factor-like protein," Proc. Natl. Acad. Sci USA, 80(7):1919-1923 (Apr. 1983).

Fairclough, R.J. et al., Radioimmunoassay of 13, 14-dihydro-15-keto prostaglandin F in bovine peripheral plasma; Prostaglandins10 (2): pp. 266-272 (1975).

Fuchs, T. et al., ["Dirt tattooing following an explosion in a chemistry class,"] Derm. Beruf Umwelt [Occupational and Environmental Dermatoses], 32(4):pp. 138-140 (1984); (provided as English language abstract).

Greenhalgh, D.G., "The role of growth factors in wound healing," J. Trauma, 41(1):pp. 159-167 (Jul. 1996).

Houck, J.C. et al., "Induction of collagenolytic and proteolytic activities by anti-inflammatory drugs in the skin and fibroblast," Biochem. Pharmacol., 17(10), 2081-2090 (Oct. 1968).

Jullien, P. et al., "Acidic cellular environments: Activation of latent TGF-β and sensitization of cellular responses to TGF-β and EGF," Int. J. Cancer, 43(5): pp. 886-891 (May 15, 1989).

Loskutoff, "Effects of acidified fetal bovine serum on the fibrionlytic activity and growth of cells in culture", J. Cell Physiology 96: pp. 361-369 (1978).

Nishida, T. et al., "Fibronectin: A new therapy for corneal trophic ulcer", Arch. Opthalmol., 101(7): pp. 1046-1048 (Jul. 1983).

Poon, A.C. et al. "Autologous serum eyedrops for dry eyes and epithelial defects: clinical and in vitro toxicity studies", British Journal of Ophthalmol 2001; 85: pp. 1188-1197 (2001).

Volchegorskii, I.A. et al, [Changes in the antioxadative activity of blood serum in inflammation], Vopr Med Khim, vol. 43, No. 4, pp. 233-238 (1997) (Abstract only).

Wysocki, A. et al., "Topical fibronectin therapy for treatment of a patient with chronic stasis ulcers", Arch. Dermatol., 124(2): pp. 175-177 (Feb. 1988).

Yawei Liu et al., "Fibroblast proliferation due to exposure to a platelet concentrate in vitro is pH dependent", Wound Repair and Regeneration, 10(5): pp. 336-340 (2002).

Saucier, Sandra E., Non-Final Office Action for U.S. Appl. No. 11/808,841, United States Patent and Trademark Office, pp. 1-6; Jun. 19, 2006.

Cho, Hee Won, International Search Report for International Patent Application No. PCT/KR03/00922; Korean Intellectual Property Office; pp. 1-2; Sep. 26, 2003.

Won Ho Joon, International Preliminary Examination Report for International Patent Application No. PCT/KR03/00922; pp. 1-7; Aug. 24, 2004.

Gollamundi, Sharmila S., Non-Final Office Action for U.S. Appl. No. 11/210,619, United States Patent and Trademark Office, pp. 1-12; Mar. 15, 2007.

Gollamundi, Sharmila S. Non-Final Office Action for U.S. Appl. No. 11/476,543, Untied States Patent and Trademark Office, pp. 1-12; Mar. 16, 2007.

Richards, Robert E., Response to Non-Final Office Action of Mar. 16, 2007 for U.S. Appl. No. 11/476,543, pp. 1-34, Jul. 31, 2007.

Golamundi, Sharmila S., Notice of Allowance for U.S. Appl. No. 11/476,543, pp. 1-10, Oct. 2, 2007.

Rempp, G., Supplementary European Search Report for European Patent Application No. EP 03723433; pp. 1-3, Jun. 22, 2006.

Bayrak, Sinasi, First Examiner's Report for European Patent Application No. EP 03723433; pp. 1-4, Jul. 19, 2007.

Schiweck, Wolfram, Response to Examiner's Report of Jul. 19, 2007 for European Patent Application No. EP 03723433; pp. 1-11, Nov. 27, 2007.

\* cited by examiner

METHOD OF TREATING A WOUND WITH ACIDIFIED PLASMA OR SERUM

CROSS-REFERENCE TO RELATED APPLICATIONS

The present application is a continuation of application Ser. No. 10/508,841, filed Sep. 21, 2004, now abandoned which claims priority to PCT/KR03/00922 filed May 9, 2004.

TECHNICAL FIELD

The present invention relates to the use of blood plasma or serum as an agent for the treatment of wounds. More specifically, the present invention relates to a pharmaceutical composition for the treatment of wounds comprising blood plasma or serum and a method for treating wounds effectively by applying said composition to a wound site to normalize the tissue-environment around the wound site.

BACKGROUND ART

The early studies on the treatment of wounds have laid emphasis on a close examination of the functions of the cell stage, i.e., the functions of inflammatory cell and platelet [Allgower M. and Hulliger L., Surgery, 47, 603 (1960); Dicoreto P. E. and Browen-Pope D. F., Proc. Natl. Acad. Sci. USA, 80, 1919 (1983); and Houck J. C. et al., Biochem. Pharmacol., 17, 2081 (1968)].

Recently, growth factors to promote tissue growth have been used in the treatment of wounds such as chronic ulcers. The growth factors stimulate mitogenesis, which is the proliferation of cells such as fibroblast. The growth factors also stimulate angiogenesis, resulting in the ingrowth of new blood vessels. Moreover, the synthesis of collagen and extracellular matrix proteins is stimulated by the growth factors (L. Greenhalgh, J. Trauma 41:159 (1996)).

Cytokines have been found as growth factors associated with wound healing. Representative examples of such cytokines include basic fibrogrowth factor which is produced by keratinocytes and fibroblasts and promotes the growth of epithelial cells; platelet-derived growth factor (PDGF) which is produced by platelets and the endothelium and other cell types and promotes the abnormal proliferation of epithelial cells in association with epidermal growth factor (EGF); transforming growth factor-β (TGF-β) which is produced by fibroblasts and platelet and promotes the growth of connective tissue; epithelial cell-growth factor which is generated in salivary glands-stimulatory glands and promotes the proliferation of epithelial cells; fibroblast growth factor (FGF); and interleukin-1 which is produced by macrophages and epithelial cells and promotes the growth and mobility of epithelial cells. Becaplermin is a genetically engineered recombinant PDGF that is commercially available as an agent for the treatment of wounds in topical formulations by Johnson & Johnson under the trade name of Regranex®. EP 0 575 484 B1 discloses a pharmaceutical composition for the regeneration and repair of mammalian tissues which includes PDGF and dexamethasone. U.S. Pat. No. 5,981,606 discloses a pharmaceutical composition for treating wounds which includes TGF-β. WO 96/30038 discloses a pharmaceutical composition for wound healing which includes TGF-β and fibric acid together with antioxidants. U.S. Pat. No. 5,183,805 discloses a pharmaceutical composition having the effect of the regeneration of tissues which includes EGF. Japanese Patent No. 05070365 and U.S. Pat. No. 6,165,978 disclose wound healing formulation containing FGF.

Formulations utilizing hyaluronic acid as an active agent have also been reported as being useful in the treatment of skin ulcers (See U.S. Pat. No. 5,897,880). Formulations including sodium hyaluronate are marketed by LAM Pharmaceutical Corporation under the trade name of IPN Wound Gel®.

Topically applied fibronectin (glycoprotein found in blood plasma) has also been reported as being useful for increasing the rate of wound healing in corneal wounds (Nishida, Larch Opthalmology 101:1046 (1983)) and leg ulcers (Wysocki et al., Arch. Dermatol. 124:175 (1988)).

Although such treatments provide some patients with partial wound relief, they need long healing time and fail to exhibit optimum response to the treatment. As wounds, especially, chronic skin ulcers, become serious clinical problems, much effort has been made in finding effective treatments of the wounds. The underlying causes responsible for poor wound closure are complex and still poorly understood.

Therefore, it would be desirable to develop new and improved methods of treating wounds. Use of the present formulations either alone or in combination with various known therapeutic agents overcomes the limitations of the prior art.

SUMMARY OF THE INVENTION

The inventors of the present invention have surprisingly found that blood plasma or serum is highly effective in the treatment of wounds. We found that partial defect wounds could be healed in several days after application of the formulation containing blood plasma or serum according to the present invention. We more surprisingly found that large full defect wounds could be healed within several weeks (about 2 to 6 weeks) after application of the formulation containing blood plasma or serum according to the present invention. These findings represent very significant improvements in both response to treatment and healing time over conventional treatments or other therapeutics currently available or reported until now.

In one aspect, the present invention provides a pharmaceutical composition for wound healing which comprises a pharmaceutically effective amount of blood plasma or serum in combination with a pharmaceutically acceptable carrier.

In another aspect, the present invention provides a method of treating wounds of a subject which comprises applying a pharmaceutical composition comprising a pharmaceutically effective amount of blood plasma or serum to the wound of the subject in need of such treatment.

DETAILED DESCRIPTION OF THE INVENTION

Figure 1:
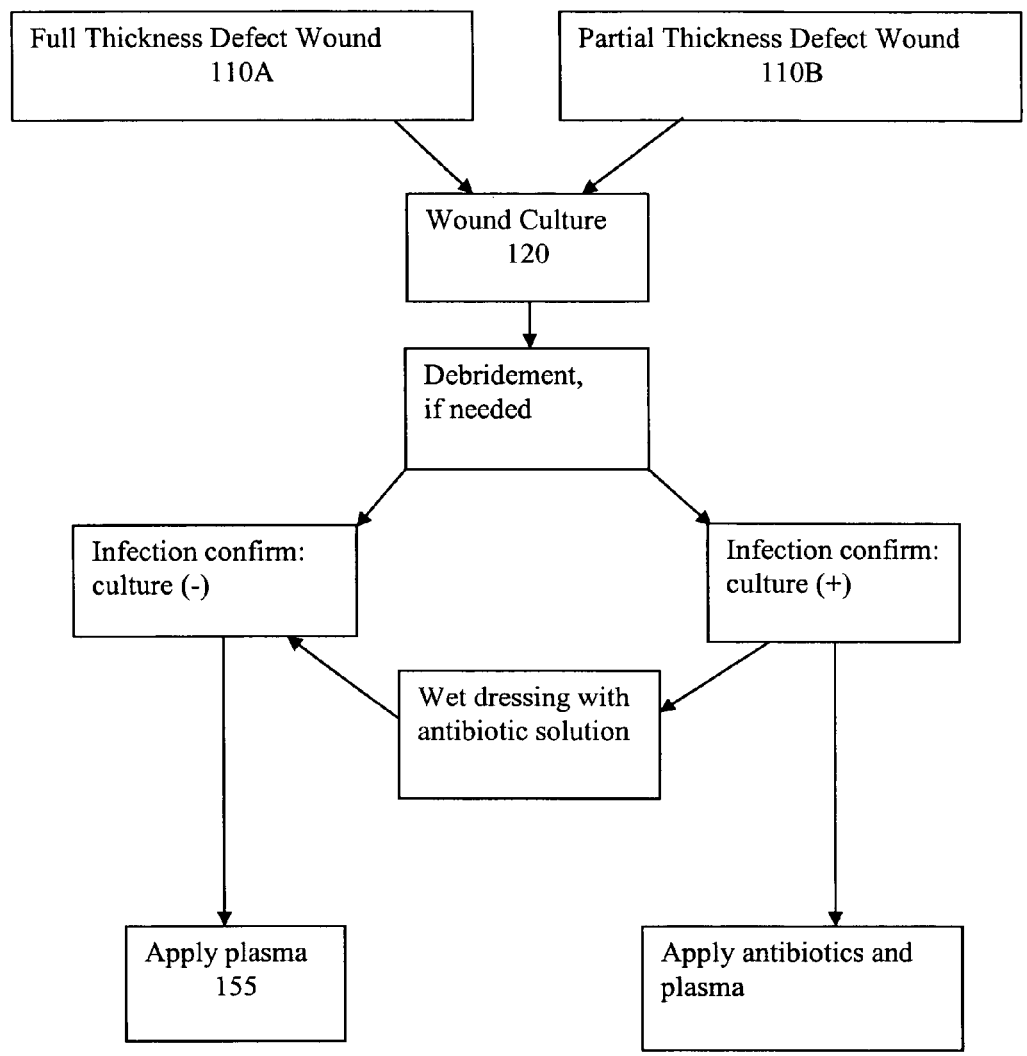
FIG. 1 shows a protocol for treatment of chronic wounds according to one or more embodiments of the present invention.

The present invention generally relates to the use of blood plasma or serum which is useful for treating wounds. The blood plasma or serum used as an active agent in a pharmaceutical composition according to the present invention is highly effective in the treatment of wounds.

Wounds are damaged conditions of living bodies and encompasses cut or disrupted pathological conditions of tissues constituting the internal and external surface of the living body, for example skin, muscle, nervous tissue, bone, soft tissue, inner organs and vascular tissue. The exemplary wounds include, but are not limited to, contusion or bruise, non-healing traumatic wounds, tissue disruption by irradiation, abrasion, gangrene, laceration, avulsion, penetrated wound, gun shot wound, cutting, burn, frostbite, cutaneous ulcers, xeroderma, skin keratosis, breakage, rupture, dermatitis, dermatophytosis, surgical wounds, wounds caused by vascular disorders, corneal wounds, sores such as pressure sore and bed sore, diabetes and poor circulation-associated conditions diabetic skin erosion, chronic ulcers, suture site following plastic surgery, spinal traumatic wounds, gynecological wounds, chemical wounds and acne. Any damaged or injured part of the living body is within the definition of the wounds. In this respect, the composition comprising blood plasma or serum according to the present invention can be useful for the repair, replacement alleviation, acceleration, promotion, healing and/or curing of any damaged or injured tissue.

Blood plasma used as an active ingredient in the composition of the present invention typically indicates the straw-colored liquid portion remaining after the material bodies such as blood cells and cell fragments were separated out from the blood. The components of the plasma are well known in the art (Philip Westerman, Plasma Proteins, VII-1 to VIII-13, Sep. 17, 2002; and Wendy Y. Craig, et al., Plasma Proteins Pocket Guide, Foundation for Blood Research— each of which is incorporated by reference in its entirety). Serum is also well defined and generally called as blood plasma without fibrinogen and other clotting factors.

The source of blood plasma or serum used in the composition of the present invention includes humans and mammalian species, for example, primates, rodents and livestock such as sheep, goat, pig, horse, dog and cattle.

The blood plasma or serum used in the present invention can be readily obtained from the blood using conventional methods such as centrifugation, sedimentation and filtration. Centrifugation would be carried out under any conditions suitable to sediment blood cells and cell fragments, e.g., about 3,000 rpm for about 10 minutes. This condition is sufficient to remove substantially all cell fragments (platelets) as well as red and white blood cells.

The supernatant plasma can be easily separated from the centrifuged cells by standard techniques. Such separation can be achieved using filtration by passing the supernatant plasma through a suitable filter. The filters include a microporous membrane through which proteins are well penetrated.

Blood plasma or serum can be fresh liquid plasma or liquid preparation obtained by centrifugation or sedimentation of whole blood. In addition, blood plasma or serum are known to be reserved in various forms prior to use, including fresh-frozen preparation, cryoprecipitated preparation, lyophilized preparation or concentrated preparation. Such all forms of plasma or serum can be used for the present invention. The fresh-frozen plasma is obtained by centrifuging the blood at about 2,800 rpm for 15 minutes to separate out blood cells and cell fragments and freezing the remaining liquid portion at the temperature of from about −18° C. to −40° C. The centrifugation is carried out within six hours from blood collection. For the use, fresh-frozen plasma is thawed out in warm water at the temperature of from about 30° C. to 37° C.

The cryoprecipitated plasma is obtained by thawing out one unit of a fresh-frozen plasma at the temperature of 4° C. to form white precipitate (cold precipitated protein) (including large amounts of factors such as VIII:C, fibrinogen, XIII and fibronectin), isolating the formed precipitate and refreezing it at the temperature of from about −18° C. to −40° C. For its use, the cryoprecipitated preparation is thawed out by putting in a refrigerator at the temperature of from 1° C. to 6° C. overnight. It may be put in a water bath at the temperature of about 4° C. to melt down more rapidly. The concentrated plasma is obtained by separating plasma from whole blood, concentrating the separated plasma by mixing it with a thickener such as dextranomer, SEPHADEX, dextramine, polyacrylamide, BIO-GEL P, silica gel, zeolite, DEBRISAN, crosslinked agarose, starch and alginate gel and discarding the remaining thickener.

In one embodiment of the present invention, the blood plasma or serum used for the present invention can be those commercially available, for example, powdered preparations purchased from blood banks. These preparations are derived from units of human blood plasma, which have been tested to elicit no antigen-antibody reaction, for example, non-reactive for antibodies to hepatitis B surface antigen (HBsAg) and hepatitis C (HCV) antibody and negative for antibodies to HIV-1 and HIV-2 viruses. All units of blood plasma or serum used to prepare such preparations are certified free of pathogens.

To reduce the potential risk of transmission of infectious agents, the preparation may be treated with an organic solvent/detergent mixture, for example, tri(n-butyl)/phosphate/polysorbate 80 designed to inactivate enveloped viruses such as HIV, hepatitis B and HCV. The inactivation and removal of viruses can be enhanced by additionally performing a nanofiltration step.

In another embodiment, the plasma or serum preparation can be prepared through purification, i.e., using solvent detergent and nanofiltration, or pasteurization of a liquid plasma fraction. Alternatively, the whole blood may be purified. The resultant plasma or serum fraction can be powdered by heating, lyophilization or other suitable drying techniques. By way of example only, blood plasma is freeze-dried at the temperature of less than −40? for several days (e.g., about 7 days). Any conventional techniques and parameters known to those of skill in the art may be used.

In another further embodiment of the present invention, the blood plasma or serum may be in the form of sheet in addition to powder. The sheet is produced by putting the plasma or serum into an appropriate template and dehydrating it. In still another further embodiment, the sheet can be provided with mechanical strength and/or physical integrity by incorporating a thickening agent or carrier into the blood plasma or serum fraction.

In a preferred embodiment of the present invention, blood plasma or serum adjusted to acidic pH. We found that the acidified blood or serum has a superior wounds healing efficacy to weakly alkaline plasma or serum. Preferably, the plasma or serum has acidic pH values of from about 3.5 to 6.5. The blood plasma or serum can be acidified using pharmaceutically acceptable inorganic or organic acids. The examples of the pharmaceutically acceptable inorganic acid include, but are not limited to, hydrochloric acid, nitric acid, sulfuric acid and phosphoric acid. The examples of the pharmaceutically acceptable organic acids include, but are not limited to, formic acid, acetic acid, trifluoroacetic acid, phthalic acid, fumaric acid, oxalic acid, tartaric acid, maleic acid, citric acid, succinic acid, malic acid, benzenesulfonic acid and p-toluenesulfonic acid.

According to the present invention, the blood plasma or serum in the form of liquid or powder can be applied directly onto the wound, i.e., sprinkled over the wound site. The plasma in the form of sheet may be applied over the wound site, which is then dressed suitably to protect the wound and prevent the healing effects of the active ingredient from diminishing. Any commercially available or conventional wound dressing may be used in the present invention. The examples of commercially available wound dressings include, but are not limited to, Compeel, Duoderm, Tagaderm and Opsite.

The composition containing a pharmaceutically effective amount of blood plasma or serum in combination with a pharmaceutically acceptable carrier can be formulated into a variety of forms by means known in the pharmaceutical art. The administration forms include, but are not limited to, conventional dosage forms of external preparation, e.g., liquid paints, sprays, lotions, creams, gels, pastes, liniments, ointments, aerosols, powders and transdermal absorbers. Actual methods for preparing administrable compositions will be known or apparent to those skilled in the art and are described in more detail in such publications as Remington's Pharmaceutical Science, 15$^{th}$ Edition, 1975, Mack Publishing Company, Easton, Pa. 18042 (Chapter 87: Blaug, Seymour), the contents of which are incorporated herein by reference.

In the external preparation of the present invention, suitable carriers can be chosen depending on the dosage forms and include, but are not limited to, hydrocarbons such as vaseline, liquid paraffin, and plasticized hydrocarbon gel (plastibase); animal and vegetable oils such as medium-chain fatty acid triglyceride, lard, hard fat, and cacao oil; higher fatty acid and alcohols and esters thereof such as stearic acid, cetanol, stearyl alcohol, and palmitic acid isopropyl; water-soluble bases such as Macrogol (polyethylene glycol), 1,3-butylene glycol, glycerol, gelatine, white sugar, and sugar alcohol; emulsifiers such as glycerine fatty acid ester, stearic acid polyoxyl, and polyoxyethylene/or curing castor oils; thickeners such as acrylic acid esters, and sodium alginates; propellants such as liquefied petroleum gas, and carbon dioxide; and preservatives such as paraoxybenzoic acid esters. The external preparation of the present invention can be prepared with the aforementioned carriers by methods well-known to those skilled in the art. In addition to said carriers, additives such as stabilizers, pigments, coloring agents, pH adjusting agents, diluents, surfactants, and antioxidants are, if necessary, used. The external preparation of the present invention can be applied to the tropical wound site by conventional methods.

The external preparation according to the present invention may be also used in adhesion onto a solid support such as a wound covering release layer. The adhesion is achieved by saturation of the solid support with the blood plasma or serum fraction, followed by dehydration of the fraction. In one embodiment of the present invention, the solid support is first coated with an adhesion layer to improve the adhesion of the blood plasma or serum to the solid support. Exemplary adhesion materials include polyacrylate and cyanoacrylate. As such formulation, there is provided a number of commercially available products, including bandage having non-adhesive wound-covering release layer in a perforated plastic film by Smith & Nephew Ltd., BAND-AID in thin strip, patch, spot and thermoplastic strip forms by Johnson & Johnson, CURITY and CURAD ("ouchless" type of bandage) by Kendall Co. (a division of Colgate-Palmolive Company), and STIK-TITE (elastic strip) by American White Cross Labs, Inc.

In one embodiment, the pharmaceutical composition according to the present invention can be formulated into a liquid paint preparation by mixing powdered plasma or serum with physiologic saline at a fixed ratio by volume and adjusting the pH value of the resulting mixture to the range of from 3.5 to 6.5. In another embodiment, time pharmaceutical composition according to the present invention can be formulated into an ointment preparation by mixing the powdered plasma or serum with a water-soluble ointment base and adding physiologic saline to the resulting mixture. Preferably, the pH value of the ointment is adjusted to the range of from 3.5 to 6.5.

According to the present invention, pharmaceutical carriers such as gels or microspheres may be used to promote the wound healing. A variety of microspheres of a polymer as carriers for one or more pharmaceutically or cosmetically active substances is described in U.S. Pat. No. 5,264,207, WO 2000/24378, WO96/13164 and WO 94/13333, the entire contents of which are incorporated herein by reference.

The pharmaceutical composition of the present invention can be used to treat a variety of wounds in mammalian animals. Especially, the composition of the present invention is effective for the treatment of non-healing ulcers, including those due to infection, malignancy, large vessel arterial insufficiency, small vessel arterial insufficiency, deep venous blockage or insufficiency, superficial venous insufficiency (varicose veins), lymphatic obstruction, intrinsic circulatory insufficiency, hematologic abnormalities, collagen vascular disorders, radiation dermatitis, trophic causes and the like.

A particular condition that can be treated with the pharmaceutical composition of the present invention includes radiation ulcers. Radiotherapy (for example, in the treatment of cancer) often leads to non-healing skin ulcers. Such ulcers do not respond well to conventional therapies as a result of poor circulation in the radiated tissue and are often treated with low intensity laser irradiation. Radiation ulcers respond well to treatment with the composition comprising the blood plasma or serum according to the present invention. In one embodiment of the present invention, 1 gm dose of the composition containing 5% by weight of blood plasma or serum is applied to a 5 cm$^2$ surface area having a thickness of from about 1.5 to 2 mils.

The pharmaceutically effective amount of the blood plasma or serum contained in the composition of the present invention refers to an amount which normalizes various cell-activating substances and abnormal cells around the wound site and promotes the wound healing. As one or skill in the art will appreciate, the amount may vary depending on the wound type being treated, the wound site to be treated, the frequency and time of administration, the route and form of administration, the severity of the wound being treated, the kinds of vehicles, and other factors.

Generally, 2 to 5% by weight of powdered blood plasma or serum are administered per dose. The frequency of administration may range between twice daily and once per week. In a specific embodiment, full thickness defect wounds are treated with from 0.01 to 0.1 g/cm$^2$ of the pharmaceutical composition of the present invention daily, preferably from 0.02 to 0.09 g/cm$^2$, more preferably from 0.02 to 0.07 g/cm$^2$.

An exemplary protocol 100 for the treatment of chronic non-healing wound is shown in FIG. 1. A defect wound is evaluated for determination of suitability for treatment with the active ingredient of the present invention, as shown in step 110 of FIG. 1. The treatment is appropriate for full thickness defect wounds such as diabetic ulcers, radiation ulcers, pressure sore, third degree burns and other tissue necrosis. The treatment is also appropriate for partial thickness defect wounds such as second degree burns, radiation dermatitis and tissue damaged during dermabrasion.

Once a defect wound is identified as suitable for the treatment according to the invention, the wound is cultured (step 120) to determine whether infection is present. The wound tissue is debrided, if needed. Stage 4 ulcers require debridement; some ulcers may also require deeper surgery. When the ulcers are filled with pus and necrotic debris, application of dextranomer beads or other hydrophilic polymers may hasten the tissue debridement without surgery. Conservative debridement of necrotic tissue with forceps and scissors should be instituted. Some debridement may be done by cleansing the wound with 1.5% hydrogen peroxide. Net dressings of water (especially whirlpool baths) will assist in debriding. The granulation that follows removal of necrotic tissue may be satisfactory for skin grafts to cover small areas.

When the culture is positive, the wound is treated for the infection (step 140). Wet dressing including an antibiotic (step 145) may be applied prior to blood plasma or serum treatment, or a formulation including powdered plasma or serum in combination with antibiotic is applied (step 148). Exemplary antibiotics include, but are not limited to, penicillinase-resistant penicillin or cephalosporin.

Where the culture is negative (step 150), no antibiotics need to be applied, and the wound is treated with the powdered plasma or serum of the invention (step 155).

The powdered plasma or serum is applied to the wound in any of a variety of formulations disclosed herein, and the wound is dressed with conventional wound dressings, such as Compeel, Duoderm, Tagaderm or Opsite wound dressings. Depending on the amount of blood plasma or serum to be administered and the desired release profile of the blood plasma or serum from the pharmaceutical carrier, dressings are changed at intervals ranged between 1 day and 5 days, and may be changed at intervals of 3-4 days. Depending on the extent of damage to the underlying tissue, healing of partial thickness defect wounds is observed in as little as 4 days and of full thickness defect wounds in as little as 2-4 weeks.

The present invention will be more specifically illustrated by the following examples. The following examples are provided to illustrate the present invention, but are not intended to be limited.

EXAMPLES

Example 1

Preparation of Blood Plasma in Liquid Phase

A human fresh-frozen blood plasma preparation (Central Blood Center of The Republic of Korea National Red Cross, Seoul, Korea), which was certified negative for pathogens including HIV, HCV and hepatitis B, was thawed out at the temperature of 30° C. and then mixed with physiologic saline at the ratio by volume of 10:1. The pH of the resulting mixture was adjusted to the value of 5.5 by adding 1N HCl or 1N NaOH with stirring to afford the desired liquid plasma. The pH value was measured using the Orion pH Meter.

The remaining blood plasma preparation was cryopreserved in lyophilization bottles, vials, containers or trays, or in other storage bottles.

Example 2

Preparation of Lyophilized Blood Plasma in Powder Form

A human fresh-frozen blood plasma preparation (Central Blood Center of The Republic of Korea National Red Cross, Seoul, Korea), which was certified negative for pathogens including HIV, HCV and hepatitis B, was thawed out at the temperature of 30? . . . 500 ml of the resulting liquid blood plasma was placed into a lyophilization bottle and then frozen at the temperature of −80° C. (Deep Freezer, Forma Science, Inc., Ohio, USA) for 8 hours. The frozen bottle was mounted on a freeze drying/lyophilization system (Labconco Corporation, Kansas City, Mo., USA) and lyophilized at the temperature of −48° C. for 7 days. All processes were under sterile conditions. 500 ml of liquid blood plasma provides approximately 30 g of lyophilized plasma powder.

Example 3

Preparation of Ointment Formulation 5 g of plasma powder prepared as described in Example 2 was mixed with 95 g of water-soluble ointment base (SAM-A base, SAM-A Pharmaceutical Ind. Co., Ltd., Seoul, Korea).

A proper quantity of physiologic saline was added to the resulting mixture with stirring to afford the desired ointment. The ointment base consists of 38 mg of sperm wax, 116 mg of stearyl alcohol, 38 mg of polyethylene glycol 4000, 192 mg of concentrated glycerine, 23 mg of cetanol, proper quantity of purified water, 9 mg of sodium lauryl sulfate, 0.87 mg of paraoxybenzoic acid ethyl and 0.12 mg of paraoxybenzoic acid butyl, based on 1 g of the base.

Example 4

Preparation of ph-Adjusted Ointment 5 g of plasma powder prepared as described in Example 2 was mixed with 95 g of a water-soluble ointment base (SAM-A base, SAM-A Pharmaceutical Ind. Co., Ltd., Seoul, Korea). A proper quantity of physiologic saline was added to the resulting mixture to produce an ointment. 1N HCl or 1N NaOH was added to the ointment with stirring to afford the ointment having the pH value of 5.5, which was determined using the Orion pH Meter.

Example 5

Preparation of Lyophilized Blood Plasma in Powder Form 500 ml of fetal bovine serum (FBS, Biofluids, Inc., Rockville, Md., USA) having not greater than 0.1 ng/mg of endotoxin capacity and not greater than 30 ng/100 ml of hemoglobin capacity was placed into a lyophilization bottle and then frozen at the temperature of −80° C. (Deep Freezer, Forma Science, Inc., Ohio, USA) for 6 hours. The frozen bottle was mounted on a freeze drying/lyophilization system (Labconco Corporation, Kansas City, Mo., USA) and lyophilized at the temperature of −48° C. for 7 days to afford the desired lyophilized plasma powder. All processes were under sterile conditions.

Example 6

Preparation of Ointment 5 g of plasma powder prepared as described in Example 5 was mixed with 95 g of a water-soluble ointment base (SAM-A Pharmaceutical Ind. Co., Ltd., Seoul, Korea). A proper quantity of physiologic saline was added to the resulting mixture to produce an ointment. 1N HCl or 1N NaOH was added to the ointment with stirring to afford the desired ointment having a pH 5.5, which was determined using the Orion pH Meter.

Example 7

Preparation of Gel 5 parts by weight of plasma powder prepared as described in Example 2 was mixed with 95 parts by weight of an emulsion, which consists of 38 mg of Carbopol ETD 2020, 116 mg of glycerin, 38 mg of propylene glycol, 192 mg of triethanolamine and a proper quantity of purified water, to afford a clear gel with pHs 5.8-6.0. Carbopol ETD 2020 is the mixture of acrylates and $C_{10-30}$ alkyl acrylate crosspolymer.

Experimental Example 1

Wound-healing Effect of Human Liquid Blood Plasma

The human liquid blood plasma according to the present invention as prepared in Example 1 was applied to a full thickness defect wound to histologically study whether it promotes the formation of granulation tissue on the wound. Ten adult white Sprague-Dawley rats weighing 300-350 mg were used in this experiment.

The animal abdomen was completely shaved and subjected to full thickness defect wound with the size of 10 mm×10 mm. Two wounds were created near both upper limbs, respectively. Likewise, two wounds were created near both lower limbs, respectively. Over each of the two wounds on left side upper and lower limbs, two layers of gauze with the size of 10 mm×10 mm wetted by 0.3 ml of liquid blood plasma having a pH 5.5 was applied. As control, over each of the two wounds on right side upper and lower limbs, two levers of gauze with the size of 10 mm×10 mm wetted by 0.3 mol of distilled water was applied. Then a dressing film (Tagaderm, 3M) was placed over that, which was sewed up on all four sides by 5/0 nylon suture so as not to be detached over the experimental period.

On day 7 after the experiment, wound tissues were taken. Biopsies were 10% neutral buffered formalin fixed for 24 hours and paraffin embedded. The paraffin-embedded biopsies were dissected 4 um in thickness. Sections were stained with hematoxyline-eosine and Masson's trichrome for the visualization of connective tissues. The width of the created granulation tissue was measured from microscopic observation at a magnification of 100× using image analysis program (Image-Pro version 3.0, Microsoft).

The thickness of the granulation tissue layer with only newly formed blood vessels was also measured. The newly formed blood vessels are those that grow from the basement of the tissue to the upper layer, i.e., longitudinally dissected blood vessels in the tissue.

In the case where sections were not of uniform thickness, those having the thickness in the middle of values list were taken. The values obtained were statistically analyzed by Student t-test.

As results, the granulation tissues of the test group were significantly thicker than those of the control group.

The trichrome staining revealed that the test group has very densely deposited collagen fibers, whereas the control group shows loose distribution of thin collagen fibers. In the test group, new blood vessels of the granulation tissues were created densely between the basement and the upper layer, indicating that the granulation tissues were grown actively. As contrast, the control group shows that a few of new blood vessels were found only at the basement of the granulation tissues, indicating that active development of the granulation tissues has not yet been initiated. The thickness of the granulation tissues was measured under the microscope using 40× magnification. The results were statistically analyzed using Student's t-test ($p<0.05$). The test group showed 168.62 μm±16.06 which was significantly different from the control group of 59.44 μm±14.42 ($p<0.01$). The values were expressed as means+/− standard deviation (SD).

Experimental Example 2

Wound-Healing Effect of Human Blood Plasma Powder

The human blood plasma powder according to the present invention as prepared in Example 2 was applied to a full thickness defect wound to histologically study whether it promotes the formation of granulation tissue on the wound.

In accordance with the same manner as described in the above Experimental Example 1, ten adult white rats were subjected to full thickness defect wound. The two wounds on left side upper and lower limbs were treated with 0.05 g of the human blood plasma powder. As control, the right side two wounds were not treated. Then a dressing film (Tagaderm, 3M) was placed over the gauzed area, which was sewed up on all four sides by 5/0 nylon suture so as not to be detached over the experimental period.

On day 7 after the experiment, the stained granulation tissue sections were prepared and then the thickness thereof was histologically viewed and measured in accordance with the same manner as described in the above Experimental Example 1. As results, the granulation tissues of the test group were significantly thicker than those of the control group.

In the trichrome staining, whereas the control group showed loosely distributed thin collagen fibers, the test group showed dense deposited collagen fibers. The development of new blood vessels in the granulation tissues of the test group was similar to that of the above Experimental Example 1 in that they were created densely between the basement and the upper layer. The thickness of the granulation tissues was measured under the microscope using 100× magnification. The results were statistically analyzed using Student's t-test ($p<0.05$). The test group showed 151.62 μm±14.24 which was significantly different from the control group of 44.24 μm±14.32 ($p<0.01$). The values were expressed as means+/− standard deviation (SD).

Experimental Example 3

Wound-Healing Effect of Human Blood Plasma-Containing Ointment

The ointment containing human blood plasma according to the present invention as prepared in Example 3 was applied to a full thickness defect wound to histologically study whether it promotes the formation of granulation tissue on the wound.

In accordance with the same manner as described in the above Experimental Example 1, ten adult white rats were subjected to full thickness defect wound. The two wounds on left side upper and lower limbs were treated with 0.3 g of the ointment of the present invention. As control, the right side two wounds were treated with 0.3 g of SAM-A base (SAM-A Pharmaceutical Ind. Co., Ltd., Seoul, Korea). Then a dressing film (Tagaderm, 3M) was placed over the gauzed area, which was sewed up on all four sides by 5/0 nylon suture so as not to be detached over the experimental period.

On day 7 after the experiment, the stained granulation tissue sections were prepared and then the thickness thereof was histologically viewed and measured in accordance with the same manner as described in the above Experimental Example 1. As results, the granulation tissues of the test group were significantly thicker than those of the control group.

In the trichrome staining, whereas the control group showed loosely distributed thin collagen fibers, the test group showed dense deposited collagen fibers. The development of new blood vessels in the granulation tissues of the test group was similar to that of the above Experimental Example 1 in that they were created densely between the basement and the upper layer.

The thickness of the granulation tissues was measured under the microscope using 100× magnification. The results were statistically analyzed using Student's t-test ($p<0.05$). The test group showed 164.50 µm±17.64 which was significantly different from the control group of 54.54 µm±10.02 ($p<0.01$). The values were expressed as means+/− standard deviation (SD).

Experimental Examples 4 and 5

Wound-Healing Effect of Fetal Bovine Serum-Containing Ointment and Powder

These experiments were conduced to study the wound-healing effect of blood plasma derived from non-human animals. The abdomens of twenty adult white rats were subjected to full thickness defect wound. In accordance with the same manner as described in the above Experimental Example 2, the first group of animals was treated with fetal bovine serum powder prepared in the above Example 5. In accordance with the same manner as described in the above Experimental Example 3, the second group of 10 animals was treated with fetal bovine serum powder prepared in the above Example 6.

On day 7 after the experiment, the stained granulation tissue sections were prepared and then the thickness thereof was histologically viewed and measured in accordance with the same manner as described in the above Experimental Examples 2 and 3. As results, the granulation tissues of the test group were significantly thicker than those of the control group.

In the trichrome staining, whereas the control group showed loosely distributed thin collagen fibers, the test group showed dense deposited collagen fibers. The development of new blood vessels in the granulation tissues of the test group was similar to that of the above Experimental Examples 2 and 3 in that they were created densely between the basement and the upper layer.

The thickness of the granulation tissues was measured under the microscope using 100× magnification. The results were statistically analyzed using Student's t-test ($p<0.05$). For the fetal bovine serum powder, the test group showed 152.62 µm±20.86 which was significantly different from the control group of 41.20 µm±7.44 ($p<0.01$).

For the fetal bovine serum-containing ointment, the test group showed 168.62 µm±19.26 which was significantly different from the control group of 58.62 Zµm±7.62 ($p<0.01$).

The values were expressed as means+/− standard deviation (SD).

Experimental Example 6

Comparison of Wound-Healing Effects Between Fetal Bovine Serum-Containing Ointment and PDGF Ointment In this experiment, the wound-healing effect of the fetal bovine serum-containing ointment prepared in the above Example 6 according to the present invention was compared to that of the Regranex® (PDGF ointment, Johnson & Johnson) which was first approved as a wound-healing agent by the FDA.

Ten adult white rats were subjected to full thickness defect wound in accordance with the same manner as described in the above Experimental Example 3 except that two full thickness defect wounds were additionally formed along the middle line of the abdomen. While the two wounds on left side upper and lower limbs were treated with 0.3 g of the ointment of the present invention, the two wounds on right side upper and lower limbs were treated with 0.3 g of Regranex®. As control, the two wounds on the middle line of the abdomen were treated with SAM-A base (SAM-A Pharmaceutical Ind. Co., Ltd., Seoul, Korea)

On day 7 after the experiment, the stained granulation tissue sections were prepared and then the thickness thereof was histologically viewed and measured in accordance with the same manner as described in the above Experimental Example 2. As results, the granulation tissues of the Regranex®-treated group were thicker than those of the control group but were thinner than those of the test group. Moreover, the granulation tissues of the Regranex®-treated group were not dense.

The trichrome staining revealed that the Regranex®-group generated only few collagen fibers, which were not different from the control group. As contrast, the test group showed densely deposited collagen fibers which were as thick as those of normal dermis and were evenly distributed. For the new blood vessels of the granulation tissues, the Regranex®-treated group showed only few longitudinally growing blood vessels. As contrast, the test group showed new blood vessels of the granulation tissues which were densely created between the basement and the upper layer.

The thickness of the granulation tissues was measured under the microscope using 200× magnification. The results were statistically analyzed using Student's t-test ($p<0.05$). The test group showed 168.62 µm±13.41 which was significantly different from the Regranex®-treated group of 81.82 µm±18.01 ($p<0.01$). The values were expressed as means+/− standard deviation (SD).

Experimental Example 7

Comparison of Wound-Healing Effects Between Human Blood Plasma-Containing Ointment and PDGF Ointment In this experiment, the wound-healing effect of the human blood plasma-containing ointment prepared in the above Example 3 according to the present invention was compared to that of the Regranex® (PDGF ointment, Johnson & Johnson). The abdomen of an adult white rat was subjected to four full thickness defect wounds. As control, the first upper wound was not treated with any agent but was well protected. The second wound was treated with 0.3 g of Regranex®. Each of the third and fourth wounds was treated with 0.3 g of the human blood plasma-ontaining ointment.

The third and fourth wounds treated with the human blood Plasma-containing ointment were even more quickly healed compared to the first non-treated wound and the second Regranex®-treated wound. FIG. 7 shows photographs of the wound sites on days 4 and 11 after the initiation of treatment. It can be seen that the plasma-treated wounds (marked as Healadex) showed onset of healing by the $4^{th}$ day and that by the $11^{th}$ day, the wounds were almost healed.

Experimental Example 8

This experiment demonstrates the healing effect of the FBS-containing ointment as prepared in the above Example 6 according to the present invention on large wounds. The second-degree burn (partial thickness defect wound) was treated with the FBS-containing ointment of the present invention. FIG. 8 showed the extent of healing on days 1, 2 and 4 after treatment. The complete wound closure was viewed on day 4 after treatment.

What is claimed is:

1. A method of treating a wound comprising applying to the wound a pharmaceutically effective amount of a composition consisting essentially of blood plasma or blood serum having a pH of 3.5 to 6.6.

2. The method of claim 1, wherein said composition consists essentially of blood plasma having a pH of 3.5 to 6.6.

3. The method of claim 1, wherein said blood plasma or blood serum is derived from livestock.

4. The method of claim 1, wherein said composition is applied to the wound in an amount of 0.01 to 0.1 $g/cm^2$.

5. The method of claim 1, wherein the composition is topically applied.

6. The method of claim 1, wherein the composition is in the form of a cream, an ointment, a gel, or a patch.

7. The method of claim 1, wherein the wound is a contusion, a bruise, a non-healing traumatic wound, a disruption by irradiation, an abrasion, a bone gangrene, laceration, an avulsion, a penetrated wound, a gun shot wound, a cut, a burn, a cold sore, a cutaneous ulcer, xeroderma, skin kefatosis, a break, a rupture, dermatitis, pain by dermatophyte, a wound by surgery, a wound by vascular disorder, a corneal wound, a pressure sore, a bed sore, a wound associated with diabetes, a chronic ulcer, a suture site, a spinal traumatic wound, a gynecological wound, a chemical wound or acne.

8. The method of claim 1, wherein wound associated with diabetes is caused by diabetic cutaneous disorder or poor circulation.

9. The method of claim 1, wherein the wound is a full thickness defect wound.

* * * * *